US00PP23111P2

(12) United States Plant Patent
Bergman

(10) Patent No.: US PP23,111 P2
(45) Date of Patent: Oct. 16, 2012

(54) *CHRYSANTHEMUM* PLANT NAMED 'CIDZ0014'

(50) Latin Name: *Chrysanthemum×morifolium*
Varietal Denomination: CIDZ0014

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/136,761

(22) Filed: Aug. 10, 2011

(51) Int. Cl.
*A01H 5/00* (2006.01)

(52) U.S. Cl. ..... Plt./295

(58) Field of Classification Search ..... Plt./295, Plt./296
See application file for complete search history.

*Primary Examiner* — Kent L Bell
(74) *Attorney, Agent, or Firm* — Joshua L. Price

(57) ABSTRACT

A new *Chrysanthemum* plant named 'CIDZ0014' particularly distinguished by the daisy-type inflorescences with yellow-orange colored ray florets, an intense brown spot in the center of the disc when grown in high light and without heat, which can develop a more yellow ray floret with less golden highlights and a greener disc if grown with higher night(heat) and day temperatures; has green foliage, good branching, and has excellent flowering uniformity.

2 Drawing Sheets

Latin name of the genus and species of the plant claimed: *Chrysanthemum×morifolium.*

Varietal denomination: 'CIDZ0014'.

BACKGROUND OF THE NEW PLANT

The present invention comprises a new *Chrysanthemum*, botanically known as *Chrysanthemum×morifolium*, and hereinafter referred to by the variety name 'CIDZ0014'.

'CIDZ0014' is a product of a planned breeding program. The new cultivar has daisy-type inflorescences with yellow-orange colored ray florets, an intense brown spot in the center of the disc when grown in high light and without heat, which can develop a more yellow ray floret with less golden highlights and a greener disc if grown with higher night(heat) and day temperatures, has green foliage, good branching, and has excellent flowering uniformity.

'CIDZ0014' originates as a natural whole plant mutation of 'Yopueblo', U.S. Plant Pat. No. 20,546. 'CIDZ0014' was discovered and selected by the inventor as a single flowering plant within a population of the parent cultivar in a controlled breeding program in Fort Myers, Fla. in March 2008. The parent cultivar 'Yopueblo' has a greyed-orange ray floret color with fewer disc florets.

The first act of asexual reproduction of 'CIDZ0014' was accomplished when vegetative cuttings were propagated from the initial selection in June 2008 in a controlled environment in Fort Myers, Fla., USA.

BRIEF SUMMARY OF INVENTION

Horticultural examination of plants grown from cuttings of the plant initiated in June 2008, and continuing thereafter, has demonstrated that the combination of characteristics as herein disclosed for 'CIDZ0014' are firmly fixed and are retained through successive generations of asexual reproduction.

'CIDZ0014' has not been observed under all possible environmental conditions. The phenotype may vary significantly with variations in environment such as temperature, light intensity and day length.

A Plant Breeder's Right for this cultivar was applied for in Canada on Aug. 17, 2010 (10-7072). 'CIDZ0014' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical inflorescence and foliage characteristics of 'CIDZ0014' with colors being as true as possible with an illustration of this type.

Figure 1:
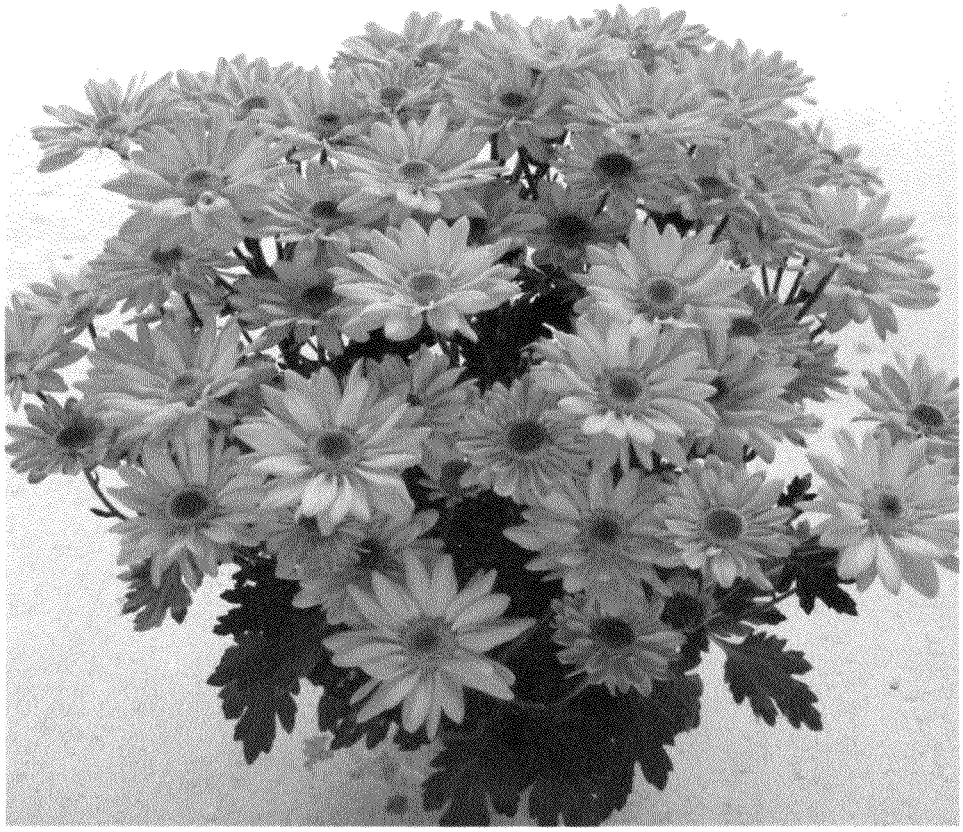
Figure 2:
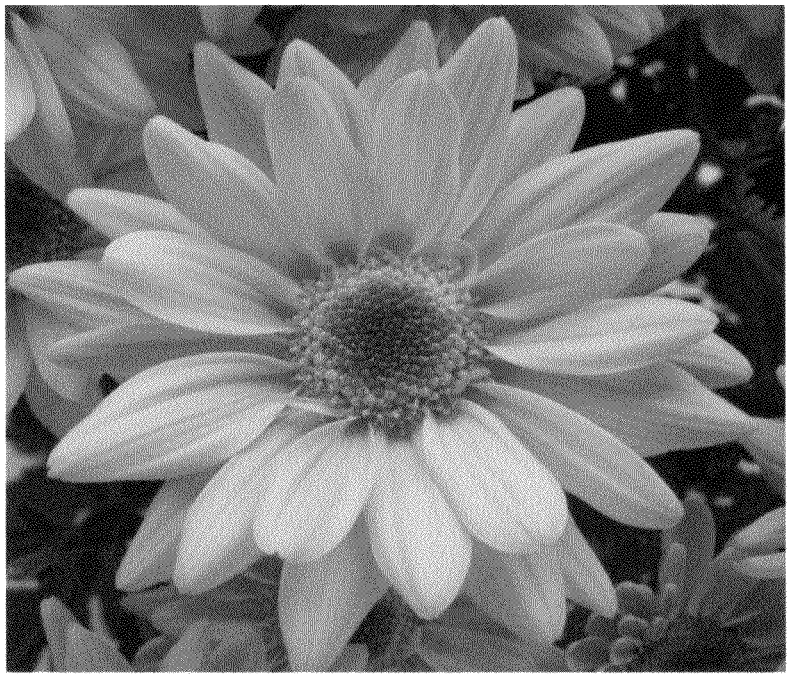

The photographic drawings show in FIG. 1., four flowering plants of the new variety growing together in a six inch pot, and in FIGS. 2. and 3., a close-up of the inflorescence.

DETAILED BOTANICAL DESCRIPTION

The plant descriptions, measurements, and aforementioned photographs of FIGS. 1. and 2. were taken in the first week of May 2011 in Gilroy, Calif. under natural light. These plants were started and grown in Nipomo, Calif. and were shipped to Gilroy, Calif. for the data collection in the first week of May 2011. These plants were approximately 11 weeks of age; grown as four plants together in a six inch pot, under greenhouse trial conditions with no supplemental heating and with high light.

Figure 3:
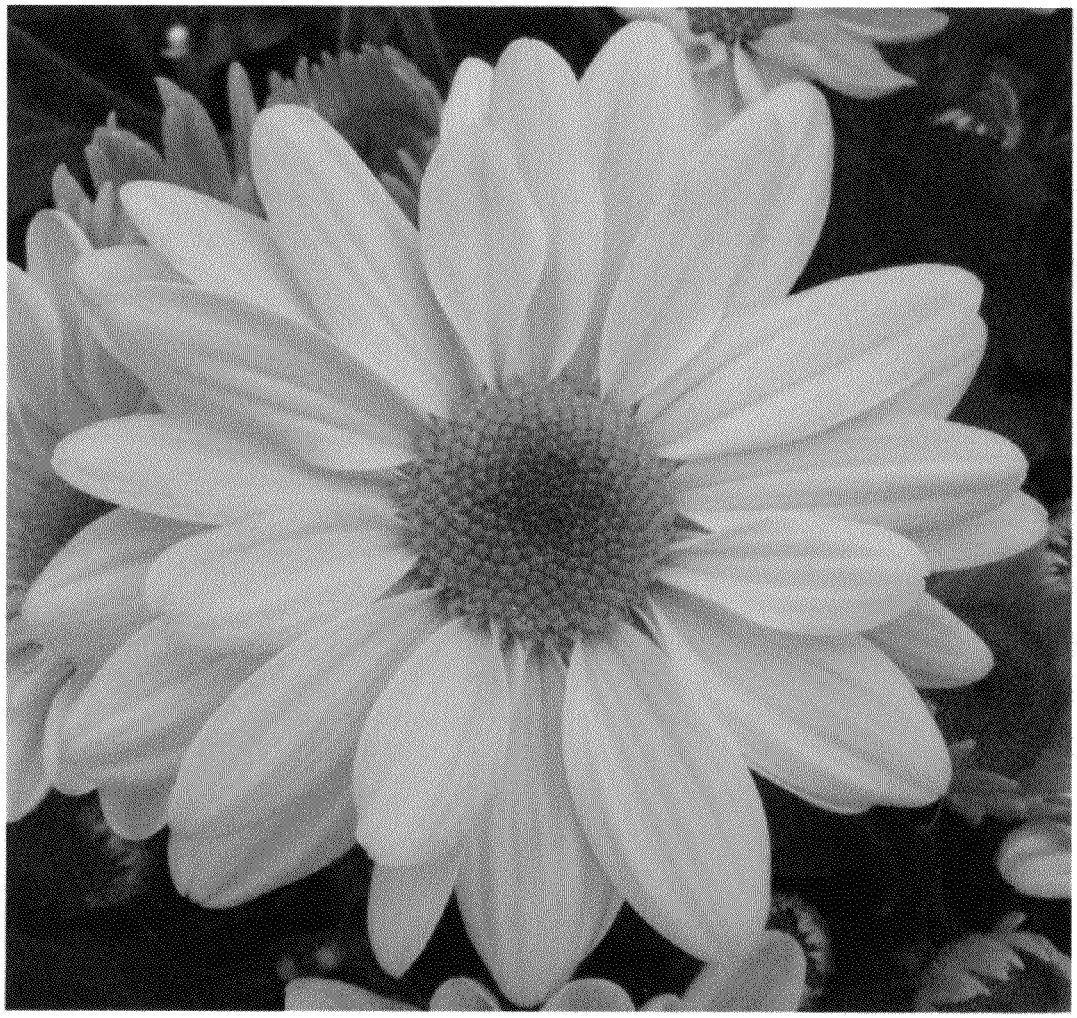

The photographs for FIG. 3. were taken in July 2011. These plants were approximately 11 weeks of age, grown in higher day and night temperatures to develop the greener discs. This photograph is used as a comparison showing the variety 'CIDZ0014' grown under two different conditions.

Color references are made to The Royal Horticultural Society Colour Chart (R.H.S.) 2001.

TABLE 1

DIFFERENCES BETWEEN THE NEW VARIETY 'CIDZ0014' AND A MOST SIMILAR VARIETY

| | 'CIDZ0014' | 'Yopueblo' (U.S. Plant Pat. No. 20,546) |
|---|---|---|
| Ray floret color: | More yellow-orange | More greyed orange |
| Quantity of disc florets: | About 300 | About 211 |
| Inflorescence diameter: | Little larger | Little smaller |

Plant:

*Form, growth and habit*.—Herbaceous pot-type, stems upright, good branching, excellent flowering uniformity.

*Plant height*.—23-25.0 cm.

*Plant height* (*inflorescence included*).—27-30.0 cm.

*Plant width*.—About 20.0 cm.

Roots:

*Number of days to initiate roots*.—About 4-5 days at about 22 degrees C.

*Number of days to produce a rooted cutting*.—About 10 days at 22 degrees C.

*Type*.—Fine, fibrous, free branching.

*Color*.—RHS N155B but whiter.

Foliage:

*Arrangement*.—Alternate, simple.

*Immature, leaf color, upper surface*.—RHS 147A but a little lighter.

*Lower surface*.—Closest to RHS 147B.

*Mature, leaf color, upper surface*.—RHS 147A but a little lighter.

*Lower surface*.—Closest to RHS 147B.

*Length*.—6.6-7.5 cm.

*Width*.—5.1-5.7 cm.

*Shape*.—Ovate.

*Base shape*.—Attenuate.

*Apex shape*.—Mucronulate.

*Margin*.—Palmately lobed; irregularly serrate.

*Texture, upper surface*.—Bifid T-shaped hairs.

*Lower surface*.—Bifid T-shaped hairs.

*Color of veins, upper surface*.—RHS 137C.

*Color of veins, lower surface*.—RHS 137C.

*Petiole color*.—RHS 137C.

*Length*.—1.7-2.0 cm.

*Diameter*.—0.3-0.35 cm.

*Texture*.—Bifid T-shaped hairs.

Stem:

*Quantity of main branches per plant*.—3-4.

*Color of stem*.—RHS 137B but appears lighter due to hairs.

*Length of stem*.—25-28.0 cm.

*Diameter*.—5-6.0 cm.

*Length of internodes*.—1.5-2.7 cm.

*Texture*.—Bifid T-shaped hairs.

*Color of peduncle*.—RHS 137A but appears lighter due to hairs.

*Length of peduncle*.—10-13.0 cm.

*Peduncle diameter*.—0.25-0.3 cm.

*Texture*.—Bifid T-shaped hairs.

Inflorescence:

*Type*.—Compositae type, solitary daisy-type inflorescences, borne terminally above foliage, ray florets arranged acropetally on a capitulum.

*Quantity of short days to flowering* (*response time*).—About 8 weeks.

*Quantity of inflorescences per plant*.—15-21.

*Lastingness of individual blooms on the plant*.—About 4 weeks.

*Fragrance*.—Slightly spicy.

Bud (just when opening/showing color):

*Color*.—RHS 2B with between RHS 20A and RHS 20B apex and RHS 1C basally.

*Length*.—1.3-1.6 cm.

*Width*.—1.2-1.5cm.

*Shape*.—Oblate.

Immature inflorescence:

*Diameter*.—3.5-5.0 cm.

*Color of ray florets, upper surface*.—RHS 3B heavily overlaid RHS 17B to RHS 17C with RHS 17A and RHS 163A in a slightly cross-hatched pattern.

*Lower surface*.—RHS 9C ground color overlaid with RHS 10C in the center with a spot of RHS 163A, and RHS 17C apex.

Mature inflorescence:

*Diameter*.—7.0-8.2 cm.

*Depth*.—1.5-2.0 cm.

*Total diameter of 'disc'*.—2.0 cm.

*Receptacle height*.—0.7 cm.

*Receptacle diameter*.—0.7-0.8 cm.

Ray florets:

*Average quantity of florets*.—31-40 in 3-4 whorls.

*Color of florets, upper surface*.—RHS 3B heavily overlaid RHS 17B to RHS 17C with RHS 17A and RHS 163A in a slightly cross-hatched pattern.

*Lower surface*.—RHS 9C ground color overlaid with RHS 10C in the center with a spot of RHS 163A, and RHS 17C apex.

*Length*.—2.5-3.5 cm.

*Width*.—0.7-1.2 cm.

*Shape*.—Elliptical.

*Apex shape*.—Obtuse to rounded, but sometimes irregularly retuse.

*Margin*.—Entire.

*Texture, upper surface*.—Papillose.

*Lower surface*.—Papillose.

Disc florets:

*Average quantity of florets*.—Approximately 300.

*Color of florets*.—RHS 1C basally with RHS 13A upper and a spot of RHS177A on the apex, which looses the dark spot upon aging.

*Floret length*.—0.5 cm.

*Width*.—0.1 cm.

*Shape*.—Tubular, elongated.

*Apex shape*.—Acute, 5 pointed.

Phyllaries:

*Quantity*.—30-35.

*Color, upper surface*.—RHS 137B.

*Lower surface*.—RHS 137A.

*Length*.—0.5-0.6 cm.

*Width*.—0.2 cm.

*Shape*.—Lanceolate.

*Apex shape*.—Acute.

*Base*.—Fused.

*Margins*.—Entire; papery with RHS 197A margins.

*Texture, upper surface*.—Glabrous.
*Lower surface*.—Bifid T-shaped hairs.

Reproductive organs:
*Pistil*.—1.
*Found on both florets*.—Yes.
*Length*.—0.5-0.6 cm.
*Style color*.—RHS 1C but more green and translucent looking.
*Style length*.—0.4 cm.
*Stigma color*.—RHS 14B.
*Stigma shape*.—Bi-parted.
*Ovary color*.—Not observed.
*Stamens*.—4.
*Found on only disc florets*.—Yes.
*Color of filaments*.—RHS 155C but more green.
*Length filaments*.—0.2-0.3 cm.
*Anther color*.—RHS 14B.
*Anther length*.—0.1 cm.
*Anther shape*.—Oblong.
*Color of pollen*.—RHS 17A.
*Pollen amount*.—Abundant.

Fertility/seed set: Fertility/seed set has not been observed on this hybrid.

Disease/pest resistance: Disease/pest resistance has not been observed on this hybrid.

What is claimed is:

1. A new and distinct variety of *Chrysanthemum* plant named 'CIDZ0014' substantially as illustrated and described herein.

* * * * *